United States Patent [19]

Ebetino

[11] Patent Number: 4,963,681
[45] Date of Patent: Oct. 16, 1990

[54] PROCESS FOR SYNTHESIS OF AMINOMETHYLENE PHOSPHONOALKYLPHOSPHINATES

[75] Inventor: Frank H. Ebetino, Norwich, N.Y.

[73] Assignee: Norwich Eaton Pharmaceuticals, Inc., Norwich, N.Y.

[21] Appl. No.: 69,663

[22] Filed: Jul. 6, 1987

[51] Int. Cl.$^5$ ................................................ C07F 9/58
[52] U.S. Cl. ...................................... 546/22; 558/157
[58] Field of Search ........................................ 546/22

[56] References Cited

U.S. PATENT DOCUMENTS

| | | | |
|---|---|---|---|
| 3,553,314 | 1/1971 | Francis | 424/49 |
| 3,683,080 | 8/1972 | Francis | 514/107 |
| 3,846,420 | 11/1974 | Wollmann et al. | 544/157 |
| 3,899,496 | 8/1975 | Schindler et al. | 546/6 |
| 3,941,772 | 3/1976 | Ploger et al. | 546/22 |
| 3,957,160 | 5/1976 | Ploger et al. | 210/58 |
| 3,979,385 | 9/1976 | Wollmann et al. | 544/157 |
| 3,988,443 | 10/1976 | Ploger et al. | 514/79 |
| 4,113,861 | 9/1978 | Fleisch et al. | 514/102 |
| 4,117,090 | 9/1978 | Ploger | 423/268 |
| 4,134,969 | 1/1979 | Schmidt-Dunker | 424/49 |
| 4,267,108 | 5/1981 | Blum et al. | 548/413 |
| 4,304,734 | 12/1981 | Jary et al. | 562/13 |
| 4,407,761 | 10/1983 | Blum et al. | 252/180 |
| 4,469,686 | 9/1984 | Andrews | 514/92 |
| 4,608,368 | 8/1986 | Blum et al. | 514/107 |
| 4,621,077 | 11/1986 | Rosini et al. | 514/108 |
| 4,687,767 | 8/1987 | Bosies et al. | 514/89 |
| 4,687,768 | 8/1987 | Benedict et al. | 514/102 |
| 4,711,880 | 12/1987 | Stahl et al. | 514/108 |
| 4,719,203 | 1/1988 | Bosies et al. | 514/108 |

FOREIGN PATENT DOCUMENTS

| | | | |
|---|---|---|---|
| 230068 | 7/1987 | European Pat. Off. | 546/22 |
| 324421 | 7/1989 | European Pat. Off. | 558/156 |
| 2360798 | 6/1975 | Fed. Rep. of Germany | 546/22 |

OTHER PUBLICATIONS

H. G. Henning et al., "Methylene-bis-phosphonic Acid Ester and Methylene-bis-phosphinic Acid Ester", 5 Z. Chem. 419 (1965).
A. N. Pudovik et al., "Reactions of Acid Ethylphosphonous and Phosphorothious Esters with Carbonylphosphonic Esters and 2,3-Butanedione", 37 Z. Obs. Khim. 876 (1967).
A. N. Pudovik et al., "Phosphonate-phosphate Rearrangement of Esters of Hydroxyalkylphosphonic Acids", 38 Z. Obs. Khim. 143 (1968).
A. N. Pudovik et al., "Synthesis and Reactions of (2-Cyanovinyl)phosphonic Esters", 38 Z. Obs. Khim. 292 (1968).
W. Ploger et al., "Preparation of 1-Aminoalkane-1,-1-diphosphonic Acids", 389 Z. Anorg. Allg. Chem. 119 (1972).
W. F. Gilmore et al., "Base-catalyzed Condensation of Aldehydes with Ethyl Bis(diethylphosphonomethyl)-phosphinate", 38 J. Org. Chem. 1423 (1973).
G. V. Romanov et al., "Thermodynamic and Kinetic Characteristics of Phosphonate-Phosphate Rearrangement", 43 Z. Obs. Khim. 2378 (1973).
Z. S. Zovikova et al., "Addition of Tetraethyl Pyrophosphite and of Tetraethyl Isohypophosphate to Compounds Containing an Activated Double Bond", 44 Z. Obs. Khim. 276 (1974).
Z. S. Zovikova et al., "Reactions of Methyl Bis(diethoxy-phosphino)acetate with Alkyl Halides", 48 Z. Obs. Khim. 757 (1978).
J. Oleksyszyn et al., "Phosphoranaloge von Aminosauren und Peptiden: Phosphon-und Phosphinanaloge von Cycloleucin", 32 Chimia 253 (1978).
L. Maier, "Herstellung und Eigenschaften von Aminomethylendiphosphinaten und -diphosphonaten, $RR^1NCH[P(O)R^2(OR^3)]_2$ und Derivitaen", 11 Phosphorus und Sulfur 311 (1981).
L. Maier, "Advances in the Chemistry of Aminophosphinic Acids", 14 Phosphorus and Sulfur 295 (1983).
Francis et al., "Chemical, Biochemical, and Medicinal Properties of the Diphosphonates", The Role of Phosphonates in Living Systems, 55 (Hildebrand, ed., 1983).
Y. Surh et al., "Technetium-99 m Labeled Phosphonic Acid Analog of Serine: Bone Uptake", 27 J. Nuclear Medicine, 847 (1986).
W. F. Gilmore et al., "Base-catalyzed Condensation of Bis(diethylphosphonomethyl)-phosphinic Amides with Aldehydes", 29 Phosphorus and Sulfur 287 (1987).
McClard et al., "Novel Phosphonylphosphinyl (P-C-P-C-) Analogues of Biochemically Interesting Diphosphates", 109 J. Am. Chemical Soc. 5544 (1987).
Biller et al., "Isoprenoid (Phosphinylmethyl)phosphonates as Inhibitors of Squalene Synthetase", 31 J. Medicinal Chemistry, 1869 (1988).

Primary Examiner—Alan L. Rotman
Attorney, Agent, or Firm—Milton B. Graff, IV; David L. Suter; Jack D. Schaeffer

[57] ABSTRACT

The present invention involves processes for making aminomethylene phosphonoalkylphosphinate compounds comprising:
 (a) heating a substantially anhydrous mixture comprising an amine, an ester of an alkyl phosphite, and an ester of a phosphate acetal; and then
 (b) adding water to the mixture.

9 Claims, No Drawings

PROCESS FOR SYNTHESIS OF AMINOMETHYLENE PHOSPHONOALKYLPHOSPHINATES

TECHNICAL FIELD

The present invention relates to processes for the preparation of aminomethylene phosphonoalkylphosphinate compounds.

BACKGROUND OF THE INVENTION

Methylene phosphonoalkylphosphinate compounds which are useful for treating abnormal calcium and phosphate metabolism are the subject of co-pending patent application of Frank H. Ebetino entitled "Methylene Phosphonoalkylphosphinates, Pharmaceutical Compositions, and Methods for Treating Abnormal Calcium and Phosphate Metabolism", Ser. No. 069,666, filed on the same day as the present patent application, published as European Patent Publication No. 298,553, on Jan. 11, 1989, the disclosure of which is hereby incorporated by reference. Some of the highly preferred compounds disclosed in this copending patent application are substituted aminomethylene phosphonoalkylphosphinates.

Certain methylene phosphonoalkylphosphinate compounds are disclosed in the following references: Gilmore, W. F., and J. W. Huber, "Base-Catalized Condensation of Aldehydes with Ethyl Bis(diethylphosphonomethyl)phosphonate", *Journal of Organic Chemistry*, Volume 38, No. 7 (1973), pp. 1423-1424; Gilmore, W. F., and J. S. Park, "Base-Catalized Condensation of Bis(diethylphosphonomethyl)phosphinic Amides with Aldehydes", *Phosphorus and Sulfur*, Volume 29 (1987), pp. 287-292; Aboujaoude, E. E., N. Collignon and P. Savignac, "Synthesis of Beta-carbonyl Phosphinates", *Journal of Organometallic Chemistry*, Volume 264 (1984), pp. 9-17; Henning, H. G., and G. Petzold, "Methylene-bis-phosphonic Acid Ester and Methylene-bis-phosphinic Acid Ester", *Z. Chem.*, Volume 5, No. 11 (1965), pp. 419-420; Abramov, V. S., and V. I. Barabanov, "Reaction of Phosphinic Acids with Aldehydes and Ketones, XXVII." *Zhurnal Obshchei Khimii*, Volume 36, No. 10 (1966), pp. 1830-1834; Abramov, V. S., V. I. Barabanov and L. I. Long, "Reactions of Phosphinic Acids with Aldehydes and Ketones, XXXII." *Zhurnal Obshchei Khimii*, Volume 37, No. 3 (1967), pp. 714-718; Pudovik, A. N., I. V. Gur'yanova, L. V. Banderova and M. G. Limin, "Reaction of Partial Esters of Ethylphosphinic and Phosphorothioic Acids with Alpha-oxo Phosphonic Acid Esters and Diacetyl", *Zhurnal Obshchei Khimii*, Volume 37, No. 4 (1967), pp. 876-881; Pudovik, A. N., I. V. Gur'yanova and M. G. Zimin, "Reactions of Phosphorus Acid, Ethylphosphinic Acid, and Thiophosphorus Acid Esters with some Substituted Benzoyl Phosphates", *Zhurnal Obshchei Khimii*, Volume 37, No. 11 (1967), pp. 2580-2585; Pudovik, A. N., I. V. Gur'yanova, L. V. Banderova and G. V. Romanov, "Phosphonate-phosphate Rearrangement of Esters of Alpha-hydroxyalkylphosphonic Acids", *Zhurnal Obshchei Khimii*, Volume 38, No. 1 (1968), pp. 143-150; Pudovik, A. N., G. E. Yastrebova, V. I. Nikitina and Y. Y. Samitov, "Synthesis and Reactions of Esters of (Beta-cyanovinyl)phosphonic Acid", *Zhurnal Obshchei Khimii*, Volume 38, No. 2 (1968), pp. 292-299; Romanov, G. V., M. S. Yafarov, A. I. Konovalov, A. N. Pudovik, I. V. Konovalova and T. N. Yusupova, "Thermodynamic and Kinetic Characteristics of the Phosphonate-phosphate Rearrangement", *Zhurnal Obshchei Khimii*, Volume 43, No. 11 (1973), pp. 2378-2386; Novikova, Z. S., S. N. Mashoshina and I. F. Lutsenko, "Addition of Tetraethyl Pyrophosphite and Tetraethyl Isohypophosphate to Compounds with Activated Multiple Bonds", *Zhurnal Obshchei Khimii*, Volume 44, No. 2 (1974), pp. 276-281; Novikova, Z. S., A. A. Prishchenko and I. F. Lutsenko, "Synthesis of 1,3-Di(oxoalkoxyphospha)cycloalkanes", *Zhurnal Obshchei Khimii*, Volume 47, No. 11 (1977), pp. 2636-2637; Novikova, Z. S., S. Y. Skorobogatova and I. F. Lutsenko, "Reaction of Tetraethyl Carbomethoxymethylene-1,1-diphosphonite with Alkyl Halides", *Zhurnal Obshchei Khimii*, Volume 48, No. 4 (1978), pp. 757-764. These references are hereby incorporated herein in their entirety. Processes for synthesizing certain phosphonoalkylphosphinate compounds are disclosed in the above references.

Processes for the synthesis of alpha-aminophosphinates are disclosed in the following references: Maier, L., "Advances in the Chemistry of Aminophosphinic Acids", *Phosphorus and Sulfur*, Volume 14 (1983), pp. 295-322; and Oleksyszyn, J., M. Soroka and J. Rachon, "Phosphoranaloge von Aminosauren und Peptiden: Phosphon- und Phosphinanaloge von Cycloleucin", *Chimia*, Volume 32, Number 7 (Jul., 1978), pp. 253-255.

SUMMARY OF THE INVENTION

It is an object of the present invention to provide novel processes for preparing certain aminomethylene phosphonoalkylphosphinate compounds.

It is a further object of this invention to provide such processes which result in aminomethylene phosphonoalkylphosphinate products having a minimal quantity of diphosphonate (bisphosphonate) impurities.

The present invention provides a process for making aminomethylene phosphonoalkylphosphinate compounds, said process comprising:

(a) heating a substantially anhydrous mixture comprising an amine, an ester of an alkyl phosphite, and an ester of a phosphonate acetal; and then (b) adding water to said mixture.

DETAILED DESCRIPTION OF THE INVENTION

The process of the present invention uses as raw materials for making certain aminomethylene phosphonoalkylphosphinate compounds an amine, an ester of an alkyl phosphite, and an ester of a phosphonate acetal. The three raw materials are combined, preferably with a small amount of a suitable solvent, to form a substantially anhydrous mixture. The mixture is heated for a period of time, then preferably cooled, and then mixed with water and allowed to react.

The term "alkyl" as used herein unless otherwise specified, means chemically-stable carbon-containing chains which may be straight, branched, or cyclic; and further which may be saturated, monounsaturated (e.g., one double bond; one triple bond), or polyunsaturated (e.g., two double bonds; two triple bonds; three double bonds; one double and one triple bond). Preferred alkyl have from 1 to about 20 carbon atoms, more preferred alkyl have from 1 to about 10 carbon atoms, and more preferred still alkyl have from 1 to about 6 carbon atoms. Still more preferred alkyl have from 1 to 4 carbon atoms, most preferred alkyl have 1 or 2 carbon atoms. "Cycloalkyls" as used herein, having from about 4 to about 10 carbon atoms are preferred; more preferred are cycloalkyls having 5 or 6 carbon atoms. Also preferred are straight chain alkyl, saturated alkyl or monounsaturated alkyl. Most preferred are straight chain, saturated alkyl.

Alkyl is preferably unsubstituted but may be substituted. Preferred substituent groups for alkyl are as follows: fluoro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; hydroxy; ether having an alkyl, heterocycle, aryl or heteroaryl group; thiol; thioether having an alkyl, heterocycle, aryl or heteroaryl group; —$SO_3H$, the pharmaceutically-acceptable salts thereof, the ester thereof derived from an alcohol of an alkyl group, the unsubstituted amide thereof, and the amide thereof substituted with one or two alkyl groups; —$CO_2H$, the pharmaceutically-acceptable salts thereof, the ester thereof derived from an alcohol of an alkyl group, the unsubstituted amide thereof, and the amide thereof substituted with one or two alkyl groups; $PO_3H_2$, the pharmaceutically-acceptable salts thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; carbamate, unsubstituted or substituted with one or two alkyl groups; peptidyl; and chemically-stable combinations thereof. More preferred alkyl substituents are halogen, especially fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; peptidyl having from one to about six amino acid moieties; and chemically-stable combinations thereof.

The term "lower alkyl", as used herein, unless otherwise specified, means unsubstituted alkyl having from 1 to about 6 carbon atoms which may be saturated or unsaturated. Preferred lower alkyl have from one to about 4 carbon atoms; more preferred lower alkyl have one or two carbon atoms. Preferred lower alkyl are saturated. Most preferred lower alkyl are methyl and ethyl. For lower alkyl groups specified herein as substituted, preferred substituents are the same as for alkyl hereinabove.

The term "heterocycle", as used herein unless otherwise specified, means chemically-stable non-aromatic rings having from about 5 to about 20 atoms, comprising at least one heteroatom selected from nitrogen, sulfur, phosphorus and oxygen. Preferred are 5 and 6 membered ring heterocycles which comprise from about 1 to about 3 heteroatoms. More preferred are 5 and 6 membered ring heterocycles which comprise one or two heteroatoms (especially nitrogen heteroatoms). Most preferred are the 6 membered ring heterocycles comprising one nitrogen atom, especially piperidinyl and piperidinylidene heterocycles. Heterocycles may be unsubstituted or substituted. Preferred heterocycles are unsubstituted or substituted with alkyl; halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; hydroxy; ether having an alkyl, heterocycle, aryl or heteroaryl group; thiol; thioether having an alkyl, heterocycle, aryl or heteroaryl group; —$SO_3H$, the pharmaceutically-acceptable salts thereof, the ester thereof derived from an alcohol of an alkyl group, the unsubstituted amide thereof, and the amide thereof substituted with one or two alkyl groups; —$CO_2H$, the pharmaceutically-acceptable salts thereof, the ester thereof derived from an alcohol of an alkyl group, the unsubstituted amide thereof, and the amide thereof substituted with one or two alkyl groups; $PO_3H_2$, the pharmaceutically-acceptable salts thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and chemically-stable combinations thereof. More preferred heterocycles are unsubstituted or substituted with lower alkyl; fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; peptidyl having from one to about six amino acid moieties; and chemically-stable combinations thereof.

The term "aryl", as used herein unless otherwise specified, means chemically-stable aromatic rings having from about 6 to about 20 carbon atoms. Preferred aryl are phenyl or naphthyl; most preferred is phenyl. Aryls may be unsubstituted or substituted. Preferred aryls are unsubstituted or substituted with alkyl; fluoro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; hydroxy; ether having an alkyl, heterocycle, aryl or heteroaryl group; thiol; thioether having an alkyl, heterocycle, aryl or heteroaryl group; —$SO_3H$, the pharmaceutically-acceptable salts thereof, the ester thereof derived from an alcohol of an alkyl group, the unsubstituted amide thereof, and the amide thereof substituted with one or two alkyl groups; —$CO_2H$, the pharmaceutically-acceptable salts thereof, the ester thereof derived from an alcohol of an alkyl group, the unsubstituted amide thereof, and the amide thereof substituted with one or two alkyl groups; $PO_3H_2$, the pharmaceutically-acceptable salts thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; carbamate, unsubstituted or substituted with one or two alkyl groups; peptidyl; and chemically-stable combinations thereof. More preferred aryl are unsubstituted or substituted with lower alkyl; fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; peptidyl having from one to about six amino acid moieties; and chemically-stable combinations thereof.

The term "heteroaryl", as used herein unless otherwise specified, means chemically-stable aromatic rings having from about 5 to about 20 atoms, comprising at least one heteroatom selected from nitrogen, sulfur, phosphorus and oxygen. Preferred are 5 and 6 membered ring heteroaryls which comprise from about 1 to about 3 heteroatoms. More preferred are 5 and 6 membered ring heteroaryls which comprise one or two heteroatoms (especially nitrogen heteroatoms). Most preferred heteroaryl is pyridinyl. Heteroaryls may be unsubstituted or substituted. Preferred heteroaryls are unsubstituted or substituted with alkyl; fluoro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; hydroxy; ether having an alkyl, heterocycle, aryl or heteroaryl group; thiol; thioether having an alkyl, heterocycle, aryl or heteroaryl group; —$SO_3H$, the pharmaceutically-acceptable salts thereof, the ester thereof derived from an alcohol of an alkyl group, the unsubstituted amide thereof, and the amide thereof substituted with one or two alkyl groups; —$CO_2H$, the pharmaceutically-acceptable salts thereof, the ester thereof derived from an alcohol of an alkyl group, the unsubstituted amide thereof, and the amide thereof substituted with one or two alkyl groups; $PO_3H_2$, the pharmaceutically-acceptable salts thereof, the ester thereof derived from an alcohol of an alkyl group, the unsubstituted amide thereof, and the amide thereof substituted with one or two alkyl groups; —($R^8$-)$PO_2H$ (where $R^8$ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; carbamate, unsubstituted or substituted with one or two alkyl groups; peptidyl; and combinations thereof. More preferred heteroaryls are unsubstituted or substituted with lower alkyl; fluoro; trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; peptidyl having from one to about six amino acid moieties; and chemically-stable combinations thereof.

The term "substituent group" as used herein means hydrogen or an alkyl, heterocycle, aryl or heteroaryl group, unless otherwise specified.

The term "chemically-stable", as used herein, refers to compounds which are sufficiently stable under normal storage and use conditions such that they can provide their intended uses. Compounds having combinations of substituents and/or moieties which would result in chemically-unstable compounds are not included in the compounds made by the processes of the present invention. Such chemically-unstable compounds are readily identified by a skilled chemist.

As used herein, an "amine" is a compound having the following chemical structure:

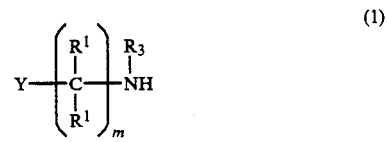

(1)

In structure (1) hereinabove, m is an integer from 0 to about 10; preferably m is from 0 to about 5; more preferably m is 0 or 1; and most preferably m is 0; and $R^3$ is hydrogen or lower alkyl.

In structure (1) hereinabove, each $R^1$ is independently selected from the group consisting of hydrogen, fluoro, lower alkyl, unsubstituted amino or the amide thereof derived from a carboxylic acid of a lower alkyl group, amino substituted with one lower alkyl group or the amide thereof derived from a carboxylic acid of a lower alkyl group, hydroxy, —$CO_2H$ or the pharmaceutically-acceptable salts thereof or the ester thereof derived from an alcohol of a lower alkyl group or the unsubstituted amide thereof or the amide thereof substituted with one or two lower alkyl groups, ether having a lower alkyl group, —$PO_3H_2$ or the pharmaceutically-acceptable salts thereof, and nitro, or two $R^1$'s on the same carbon atom are =O or =$NR^9$ (where $R^9$ is unsubstituted lower alkyl or may be hydrogen when there is another nitrogen atom attached to the same carbon atom as the =$NR^9$ moiety), or two $R^1$'s on adjacent carbon atoms may be replaced by an additional bond between the carbon atoms. (For the sake of chemical stability of the compounds of the present invention, $R^1$ cannot be such that there is a halogen and an oxygen or sulfur or nitrogen singly bonded to the same carbon atom or such that two of an oxygen or sulfur or nitrogen are singly bonded to the same carbon atom). Each $R^1$ moiety is preferably independently selected from hydrogen, methyl, ethyl, hydroxy, unsubstituted amino, or two $R^1$'s on the same carbon atom are =O or =$NR^9$ (where $R^9$ is unsubstituted lower alkyl or may be hydrogen when there is another nitrogen atom attached to the same carbon atom as the =$NR^9$ moiety), or two $R^1$'s on adjacent carbon atoms are replaced by an additional bond between the carbon atoms. Most preferred is all $R^1$ groups being hydrogen.

In structure (1) hereinabove, Y is a substituent of alkyl as defined hereinbefore. Y is preferably $Y^1$, $Y^2$ or Z as hereinafter defined.

When Y is $Y^1$, m is more preferably from 1 to about 5. The $Y^1$ moiety is preferably selected from hydrogen, fluoro, unsubstituted amino or the amide thereof derived from a carboxylic acid of a lower alkyl group, amino substituted with one lower alkyl group or the amide thereof derived from a carboxylic acid of a lower alkyl group, hydroxy, —$CO_2H$ or the pharmaceutically-acceptable salts thereof or the ester thereof derived from an alcohol of a lower alkyl group or the unsubstituted amide thereof or the amide thereof substituted with one or two lower alkyl groups. Preferred $Y^1$ is hydrogen, fluoro, unsubstituted amino or the amide thereof derived from a carboxylic acid of a lower alkyl group, amino substituted with one lower alkyl group, and hydroxy. Most preferred $Y^1$ is hydrogen, hydroxy, amino substituted with one methyl group, and especially unsubstituted amino.

When Y is Z, m is preferably from 0 to about 2; especially preferred is m being 0 or 1; most preferred is m=0. The Z moiety is selected from the group consisting of unsubstituted or substituted cycloalkyl, heterocycle, aryl and heteroaryl; with preferred Z being selected from five-membered ring heterocycles and heteroaryls having one heteroatom, five-membered ring heterocycles and heteroaryls having two heteroatoms, unsubstituted or substituted phenyl, six-membered ring heterocycles and heteroaryls having one heteroatom, and six-membered ring heterocycles and heteroaryls having two heteroatoms; and preferably all the heteroatoms in the ring are nitrogen. More preferred Z is phenyl, pyrrolidinyl, pyrrolyl, pyridinyl, piperidinyl, piperidinylidene, pyridazinyl, pyrimidinyl, pyrazinyl, and morpholinyl. Most preferred Z is pyrimidinyl, and especially piperidinyl and pyridinyl.

The Z moiety may be unsubstituted or substituted. Preferred is the Z moiety being unsubstituted or substituted on the carbon atoms of the ring with one or more substituents selected from the group consisting of lower alkyl; unsubstituted amino, and the amide thereof derived from a carboxylic acid of a lower alkyl group; amino substituted with one lower alkyl group, and the amide thereof derived from a carboxylic acid of a lower alkyl group; hydroxy; ether having a lower alkyl group; —$CO_2H$, the pharmaceutically-acceptable salts thereof, the ester thereof derived from an alcohol of a lower alkyl group, the unsubstituted amide thereof, and the amide thereof substituted with one lower alkyl group; and chemically-stable combinations thereof. Preferred is the Z moiety being unsubstituted or substituted on the carbon atoms of the ring with one or more substituents selected from the group consisting of fluoro, lower alkyl, unsubstituted amino and the acetyl amide thereof, amino substituted with one methyl group and the acetyl amide thereof, hydroxy, methyl ether, ethyl ether, —$CO_2H$ and the pharmaceutically-acceptable salts thereof, —$CO_2CH_3$, —$CO_2C_2H_5$, —$CONH_2$, —$CONHCH_3$, and —$CON(CH_3)_2$. More preferred is the Z moiety being unsubstituted, or mono-, di-, or tri-substituted independently with the preceding substituents. Most preferred is the Z moiety being unsubstituted, or mono-substituted with a substituent selected from the group consisting of methyl, ethyl, fluoro, trifluoromethyl, hydroxy, (N-methyl)amino, methyl ether, —$CO_2H$ and the pharmaceutically-acceptable salts thereof, —$CO_2CH_3$, —$CONH_2$, and especially unsubstituted amino.

When Y is $Y^2$, m is preferably 0 to about 2, more preferably 0 or 1, most preferably 0. $Y^2$ is peptidyl having the following chemical structure:

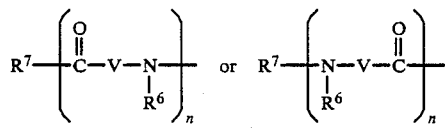
(2)

In structure (2) hereinabove, n is an integer from 1 to about 100, preferably from 1 to about 6; each $R^6$ and $R^7$ is independently hydrogen or lower alkyl, preferably each $R^6$ and $R^7$ are hydrogen; each V is independently unsubstituted or substituted lower alkyl, or independently each $R^6$ and V together with the included nitrogen atom to which they are bound, form a 5- or 6- membered ring which is unsubstituted or substituted, preferably each V or rings in which they are incorporated are moieties found in naturally-occurring amino acid moieties, i.e. lysine, leucine, isoleucine, valine, phenylalanine, arginine, histidine, methionine, alanine, aspartic acid, threonine, proline, glycine, serine, tyrosine, tryptophan, glutamine and cysteine.

As used herein, an "ester of an alkyl phosphite" is a compound having the following chemical structure:

(3)

In structure (3) hereinabove, $R^5$ is alkyl, preferably lower alkyl. R is a moiety selected from the group consisting of hydrogen, and alkyl, other than alkyl having unsaturation between the carbon adjacent the phosphorus and an adjacent carbon or nitrogen atom. Preferred R is unsubstituted alkyl, especially lower alkyl. Preferred substituents on the R alkyl, when substituted, include fluoro, unsubstituted and substituted phenyl, unsubstituted and substituted pyridinyl, unsubstituted amino, amino substituted with one lower alkyl group, hydroxy, carboxy, and combinations thereof. More preferred substituents are fluoro, phenyl, unsubstituted amino, and hydroxy; and most preferred are fluoro (especially when present as trifluoromethyl) and phenyl. Particularly preferred R moieties are selected from unsubstituted, straight-chain, saturated lower alkyl groups. Also preferred R moieties are selected from methyl, ethyl, n-propyl, iso-propyl, n-butyl, iso-butyl, sec-butyl, and tert-butyl. More preferred still R moieties are selected from methyl, ethyl, n-propyl, and n-butyl. Most preferred R moiety is methyl.

As used herein, an "ester of a phosphonate acetal" is a compound having the chemical structure:

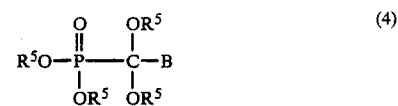
(4)

wherein $R^5$ is alkyl, preferably lower alkyl.

In structure (4) hereinabove, B is a moiety selected from the group consisting of hydrogen; fluoro; unsubstituted and substituted lower alkyl; unsubstituted and substituted cycloalkyl having from about 3 to about 7 atoms in the ring; unsubstituted and substituted heterocycle having from about 3 to about 7 atoms in the ring; unsubstituted and substituted phenyl; —$CO_2H$, the pharmaceutically-acceptable salts thereof, the ester thereof derived from an alcohol of a lower alkyl group, the unsubstituted amide thereof, and the amide thereof substituted with one or two lower alkyl groups. Preferred B is selected from the group consisting of hydrogen, fluoro, unsubstituted and substituted lower alkyl, unsubstituted and substituted phenyl, unsubstituted and substituted benzyl, and —$CO_2H$ and the pharmaceutically-acceptable salts thereof and the ester thereof derived from an alcohol of a lower alkyl group and the unsubstituted amide thereof or the amide thereof substituted with one or two lower alkyl groups. More preferred B is selected from hydrogen, methyl, ethyl, —$CO_2H$ and the pharmaceutically-acceptable salts thereof, —CO$_2$CH$_3$, and —CONH$_2$. Most preferred B is hydrogen.

The ester of a phosphonate acetal can be synthesized from trialkyl orthoformate and dialkyl chlorophosphite, as exemplified in Dietsche, W., "Darstellung von C-phosphorylierten Formaldehydacetalen", *Liebigs Ann. Chem.*, Vol. 712 (1968), pp. 21-27, which is incorporated herein by reference.

The process of the present invention is depicted schematically as follows:

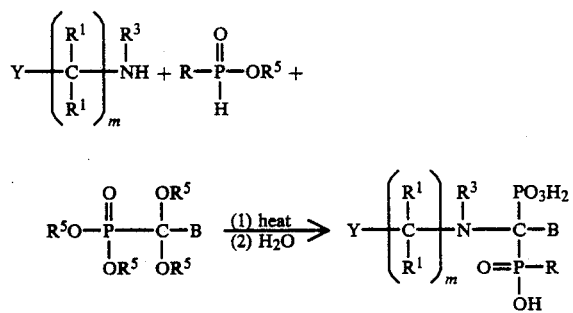

wherein m, Y, R, R$^1$, R$^3$ and R$^5$ are as described hereinbefore.

To prepare the aminomethylene phosphonoalkylphosphinates according to the process of the present invention, the amine, ester of an alkyl phosphite, and ester of a phosphonate acetal are combined in a reaction vessel. (If necessary to prevent unwanted reactions of substituents on the raw materials, suitable protecting groups may be placed on such substituents for later removal.) A small amount of solvent is preferably included in this reaction mixture; preferred solvents are alcohols having from 1 to about 6 carbon atoms; more preferred are methanol, ethanol, n-propanol and isopropanol; most preferred is ethanol. The reaction mixture is heated to a temperature which is determined for each combination of reactants; overheating causes side reactions to be accelerated, and product of unacceptable purity results. Progress of the reaction is preferably followed by determining consumption of the amine by liquid chromatography or other suitable means. The alcohol is allowed to distill off the reaction mixture. Equamolar amounts of the three reactants are preferably included in the reaction mixture.

When the reactants have been consumed in the reaction, the resulting mixture is preferably cooled and an excess of water (preferably hot water) is added to the reaction mixture. The water is added with care since this can result in an exotherm. The reaction mixture is preferably heated for a period sufficient to insure complete conversion to the phosphonophosphinic acid, preferably about one hour. The solid product is then filtered from the reaction mixture, washed with hot water, and dried.

Further product can generally be obtained by stripping the tiltrate to one-quarter to one-third of its volume, cooling it to room temperature, and allowing it to stand. The resulting crystals are filtered, washed with water and dried.

The following nonlimiting examples are provided to exemplify the processes of the present invention.

EXAMPLE 1

Synthesis of N-(2'-(3'-methyl)-pyridinyl)Aminomethane Phosphonomethylphosphinic Acid To a flask containing triethyl orthoformate (23.6 gm; 0.16 moles) equipped with a magnetic stirrer, condensor, and nitrogen atmosphere, is added diethyl chlorophosphite (25 gm; 0.16 moles) over 15-30 minutes; an extremely exothermic reaction occurs. The reaction solution is then heated at 135° C. for 3 hours. The resulting solution is distilled using a Kugelrohr distillation apparatus at 80° C. (0.01 mm Hg) to yield 32 gm of diethoxymethylphosphonic acid diethyl ester ($^{31}$P NMR 13.2 ppm).

This ester (15 gm, 62.5 mmoles) is combined with ethyl hydrogen methylphosphinate (9.6 gm; 62.5 mmoles; See Dougherty, K. E., W. A. Eychaner and J. I. Stevens, *Applied Spectroscopy*, Volume 22, No. 2 (1968), p. 95, which is incorporated herein by reference in its entirety) and 2-amino-3-methylpyridine (6.75 gm; 62.5 mmoles) in a flask equipped with a short path distillation head, magnetic stirrer, and a nitrogen atmosphere. The flask is placed in an oil bath and the temperature is slowly brought to 150° C. The reaction mixture is kept at this temperature until no further ethanol is distilled off (approximately 30 minutes), and then the mixture is heated at 170°-175° C. for 4 to 5 hours. After this time, the bath temperature is cooled to 110° C., 75 ml of water is added, and this reaction mixture is allowed to reflux for one hour. The resulting white precipitate is collected, rinsed with hot water (2×10 ml), and dried to yield 5.7 gm of N-(2'-(3'-methyl)-pyridinyl)-aminomethane phosphonomethylphosphinic acid.

The monosodium salt is prepared by the addition of one equivalent of 6N NaOH to bring a 10% aqueous solution to a pH of 4.0. $^1$H NMR (D$_2$O; 1 equivalent NaOH): 7.69(1H, d, J=7.2 Hz); 7.65 (1H, d, J=6.3 Hz); 6.8 (1H, dd); 4.0 (1H, dd, J=20.1 Hz, J=15.6 Hz); 2.23(3H, s); 1.42 ppm (3H, d, J=14.4 Hz). $^{31}$P NMR: 35.11 (d, J=15 Hz); 11.54 ppm (d, J=15 Hz). Anal. calc'd. for C$_8$H$_{14}$N$_2$O$_5$P$_2$: C=34.30; H=5.04; N=10.00. Found: C=34.54; H=5.30; N=9.79.

EXAMPLE 2

Synthesis of N-(2'-(3'-methyl)-piperidinylidene)-Aminomethane Phosphonomethylphosphinic Acid, Monosodium Salt To a 10% solution of N-(2'-(3'-methyl)-pyridinyl)-aminomethane phosphonomethylphosphinic acid is added 6N NaOH until the pH is adjusted to 4.0. The resulting solution is diluted to 820 ml water and hydrogenated for 48 hours at 50 psi at room temperature with 12 gm of 10% Pd/C in a Parr hydrogenation apparatus. The solution is then filtered and evaporated to dryness to yield 43 gm of N-(2'-(3'-methyl)-piperidinylidene)-aminomethane phosphonomethylphosphinic acid, monosodium salt. The following spectral data are reported on the 1:1 mixture of diastereoisomers. $^{31}$P NMR (2.5% in D$_2$O): 33.37 (d, J=13Hz) 32.93 (d, J=13Hz), 9.99 (d, J=13Hz), 9.66 (d, J=13Hz). $^1$H NMR (1% in D$_2$O): 3.88 (1H, dd, J=15.6, 19.9); 3.45 (2H, m); 2.92 (1H, m); 1.96 (2H, m); 1.82 (1H, m); 1.66 (1H, m); 1.46 (1.5H, d, J=14.5); 1.44 (1.5H, d, J=13.9); 1.40 (1.5H, d, J=6.9); 1.39 ppm (1.5H, d, J=6.8). $^{13}$C NMR (10% in D$_2$O): 169.6, 55.7 (2 overlapping dd's), 44.0, 33.3, 27.7, 20.6, 19.5, 17.7 (d, J=98). Anal. calc'd. for $C_8H_{17}N_2O_5P_2Na \cdot H_2O$: C=29.63; H=5.91; N=8.64. Found: C=30.06; H=6.31; N=8.77.

EXAMPLE 3

Synthesis of
N-(1-(5-amino-2-methyl-1-oxo)-pentyl)-Aminomethane Phosphonomethylphosphinic Acid A 10% aqueous solution of sodium N-(2'-(3'-methyl)-pyridyl)-amino methane-1-phosphono-1-methylphosphinate (10 g) is refluxed for 72 hours under a nitrogen atmosphere. After noting approximately a 75% conversion to new material, pure N-(1-(5-amino-2-methyl-1-oxo)-pentyl)-aminomethane-1-phosphono-1-methylphosphinic acid is isolated on a preparative HPLC silica gel column on elution with approximately 91:9 MeOH/H$_2$O. The product isolated is reported as a 1:1 mixture of diastereoisomers. $^{31}$P NMR (D$_2$O, pD=12): 35, 12 ppm. $^{13}$C NMR (10% in D$_2$O): 180.4, 52.2 (2 overlapping dd's), 42.5, 41.4, 32.4, 26.9, 19.2, 17.6 (d, J=96). $^1$H NMR (1% in D$_2$O): 4.35 (1H, m), 3.00 (2H, m), 2.55 (1H, m), 1.58 (2H, m), 1.53 (1H, m), 1.39 (1.5H, d, J=14.0), 1.36 (1.5H, d, J=14.0), 1.17 (1.5H, d, J=6.8), 1.16 (1.5H, d, J=6.8).

What is claimed is:

1. A process for making aminomethylene phosphonoalkylphosphinate compounds having the chemical structure:

$$Y-\left(\begin{array}{c}R^1\\|\\C\\|\\R^1\end{array}\right)_m \begin{array}{c}R^3\\|\\N\\|\\H\end{array} \begin{array}{c}PO_3H_2\\|\\C-B\\|\\O=P-R\\|\\OH\end{array}$$

said process comprising:
(1) heating a substantially anhydrous mixture comprising:
(a) an amine having the chemical structure:

$$Y-\left(\begin{array}{c}R^1\\|\\C\\|\\R^1\end{array}\right)_m \begin{array}{c}R^3\\|\\NH\end{array}$$

wherein
(i) m is an integer from 0 to 10;
(ii) (a) each R$^1$ is independently selected from the group consisting of hydrogen; fluoro; lower alkyl; unsubstituted amino, and the C$_1$-C$_6$ amides thereof; amino substituted with one lower alkyl group, and the C$_1$-C$_6$ amides thereof; hydroxy, —CO$_2$H and the pharmaceutically-acceptably salts, the C$_1$-C$_6$ esters, and the substituted and unsubstituted amides thereof; ether having a lower alkyl group; —PO$_3$H$_2$ and the pharmaceutically-acceptable salts thereof; and nitro; or
(b) two R$^1$'s on the same carbon atom are =O; or =NR$^9$, where R$^9$ is unsubstituted lower alkyl, or hydrogen when there is another nitrogen atom attached to the same carbon atom as the =NR$^9$ moiety; or two R$^1$'s on adjacent carbon atoms may be replaced by an additional bond between the carbon atoms;
(c) except that R$^1$'s are not such that there is a halogen and an oxygen or sulfur or nitrogen singly bonded to the same carbon atom or such that two of an oxygen or sulfur or nitrogen are singly bonded to the same carbon atom;
(iii) R$^3$ is selected from the group consisting of hydrogen and lower alkyl; and
(iv) Y is pyridyl or substituted pyridyl;
(b) an ester of an alkyl phosphite having the chemical structure:

$$\begin{array}{c}O\\||\\R-P-OR^5\\|\\H\end{array}$$

wherein
(i) R is selected from the group consisting of hydrogen, and unsubstituted and substituted alkyl; and
(ii) R$^5$ is alkyl; and
(c) an ester of an phosphonate acetal having the chemical structure:

$$\begin{array}{ccc}O & & OR^5\\|| & & |\\R^5O-P&-&C-B\\| & & |\\OR^5 & & OR^5\end{array}$$

wherein
(i) B is selected from the group consisting of hydrogen; fluoro; unsubstituted and substituted lower alkyl; unsubstituted and substituted cycloalkyl having from 3 to 7 atoms in the ring; unsubstituted and substituted phenyl; and —CO$_2$H, and the pharmaceutically-acceptable salts, the C$_1$-C$_6$ esters, and the substituted and unsubstituted amides thereof; and
(ii) R$^5$ is alkyl; and
(2) then adding water to said mixture.

2. The process of claim 1 wherein
(a) each R$^1$ is independently selected from the group consisting of hydrogen, methyl, ethyl, hydroxy, unsubstituted amino; or two R$^1$'s on the same carbon atom are =O or =NR$^9$; or two R$^1$'s on adjacent carbon atoms are replaced by an additional bond between the carbon atoms; and
(b) R$^3$ is hydrogen;
(c) each R$^5$ is lower alkyl;
(d) R is selected from the group consisting of unsubstituted lower alkyl groups and lower alkyl groups substituted with fluoro, unsubstituted and substituted phenyl, unsubstituted and substituted pyridinyl, unsubstituted amino, amino substituted with one lower alkyl group, hydroxy, or carboxy, and combinations thereof; and
(e) B is selected from the group consisting of hydrogen, methyl, ethyl, —CO$_2$H and the pharmaceutically-acceptable salts thereof, —CO$_2$CH$_3$, and —CONH$_2$.

3. The process of claim 2 wherein R is unsubstituted, straight-chain, saturated lower alkyl.

4. The process of claim 3 wherein B is hydrogen.

5. The process of claim 4 wherein
(a) m is an integer from 0 to 2; and (b) Y is unsubstituted pyridyl, or pyridyl substituted on the carbon atoms thereof with one or more substituents selected from the group consisting of fluoro, lower alkyl, unsubstituted amino and the acetyl amide thereof, amino substituted with one methyl group and the acetyl amide thereof, hydroxy, methyl ether, ethyl ether, —$CO_2H$ and the pharmaceutically-acceptable salts thereof, —$CO_2CH_3$, —$CO_2C_2H_5$, —$CONH_2$, —$CONH(CH_3)$, and —$CON(CH_3)_2$.

6. The process of claim 5 wherein
(a) m is 0; and
(b) Y is unsubstituted pyridyl or pyridyl monosubstituted with a substituent selected from the group consisting of methyl, ethyl, fluoro, trifluoromethyl, hydroxy, (N-methyl)amino, methyl ether, —$CO_2H$ and the pharmaceutically-acceptable salts thereof, —$CO_2CH_3$, and —$CONH_2$.

7. The process of claim 6 wherein Y is attached at the 2-position, and Y is unsubstituted or monosubstituted with a methyl or amino at the 3-, 4- or 5-position.

8. The process of claim 7 wherein Y is unsubstituted.

9. The process of claim 7 wherein Y is monosubstituted with methyl at the 3- or 5-position.

* * * * *